United States Patent
Fuimaono et al.

(10) Patent No.: US 7,588,568 B2
(45) Date of Patent: Sep. 15, 2009

(54) ATRIAL ABLATION CATHETER AND METHOD FOR TREATING ATRIAL FIBRILLATION

(75) Inventors: Kristine B. Fuimaono, Covina, CA (US); Irma P. Hill, La Verne, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 0 days.

(21) Appl. No.: 10/199,525

(22) Filed: Jul. 19, 2002

(65) Prior Publication Data

US 2004/0015164 A1 Jan. 22, 2004

(51) Int. Cl.
*A61B 18/18* (2006.01)
(52) U.S. Cl. .......................................... 606/41; 606/45
(58) Field of Classification Search .............. 606/27–52
See application file for complete search history.

(56) References Cited

U.S. PATENT DOCUMENTS

| | | | |
|---|---|---|---|
| 4,984,581 | A | 1/1991 | Stice |
| 5,055,109 | A | 10/1991 | Gould et al. |
| 5,125,895 | A | 6/1992 | Buchbinder et al. |
| 5,327,905 | A | 7/1994 | Avitall |
| 5,383,923 | A | 1/1995 | Webster, Jr. |
| 5,487,385 | A | 1/1996 | Avitall |
| 5,545,200 | A | 8/1996 | West et al. |
| 5,643,251 | A | 7/1997 | Hillsman et al. |
| 5,700,262 | A | 12/1997 | Acosta et al. |
| 5,800,428 | A | 9/1998 | Nelson et al. |

(Continued)

FOREIGN PATENT DOCUMENTS

EP 0 928 601 A1 7/1999

(Continued)

OTHER PUBLICATIONS

M. Haissaguerre et al., *Spontaneous Initiation of Atrial Fibrillation by Ectopic Beats Originating in the Pulmonary Veins*, The New England Journal of Medicine, vol. 339 # 10, pp. 659-666 (Sep. 3), 1998.

(Continued)

*Primary Examiner*—Roy D Gibson
(74) *Attorney, Agent, or Firm*—Christie, Parker & Hale, LLP.

(57) ABSTRACT

A catheter for ablating tissue is provided. The catheter comprises an elongated generally-tubular catheter body having proximal and distal ends and at least one lumen extending therethrough. A non-retractable ablation assembly is attached to the distal end of the catheter body. The ablation assembly comprises proximal and distal non-conductive tubings, each having a lumen extending therethrough and a generally tubular electrode mounted between the proximal and distal non-conductive tubings. The tubular electrode is formed of a material having shape-memory and has at least one irrigation port through which fluid can pass from the inside to the outside of the electrode. The ablation assembly further comprises a non-conductive protective tubing extending generally parallel to and along the outside of the tubular electrode. The protective tubing has proximal and distal ends extending into the proximal and distal non-conductive tubings, respectively. The catheter further comprises at least one of an electrode lead wire and a temperature sensor wire, and preferably both, extending through the non-conductive protective tubing and catheter body, the electrode lead wire having a distal end mounted to a ring electrode mounted on the distal non-conductive tubing, and the temperature sensor wire having a distal end mounted on or under the distal non-conductive tubing. The catheter also comprises an infusion tube extending through the catheter body and having a distal end in fluid communication with the proximal end of the tubular electrode.

26 Claims, 9 Drawing Sheets

U.S. PATENT DOCUMENTS

| | | | |
|---|---|---|---|
| 5,810,802 A * | 9/1998 | Panescu et al. | 606/31 |
| 5,833,673 A | 11/1998 | Ockuly et al. | |
| 5,876,373 A * | 3/1999 | Giba et al. | 604/95.04 |
| 5,935,124 A | 8/1999 | Klumb et al. | |
| 5,957,961 A | 9/1999 | Maguire et al. | |
| 6,033,403 A * | 3/2000 | Tu et al. | 606/41 |
| 6,096,036 A | 8/2000 | Bowe et al. | |
| 6,123,084 A | 9/2000 | Jandak et al. | |
| 6,371,955 B1 | 4/2002 | Fuimaono et al. | |
| 6,522,930 B1 * | 2/2003 | Schaer et al. | 607/101 |
| 6,569,160 B1 * | 5/2003 | Goldin et al. | 606/41 |

FOREIGN PATENT DOCUMENTS

| | | |
|---|---|---|
| EP | 1 075 820 A1 | 2/2001 |
| WO | WO 99/56812 A2 | 11/1999 |
| WO | WO 99/56812 A3 | 11/1999 |
| WO | WO 02/30310 A1 | 4/2002 |

OTHER PUBLICATIONS

European Search Report, for EP 03 25 4516, dated Mar. 29, 2004, 3 pages.

* cited by examiner

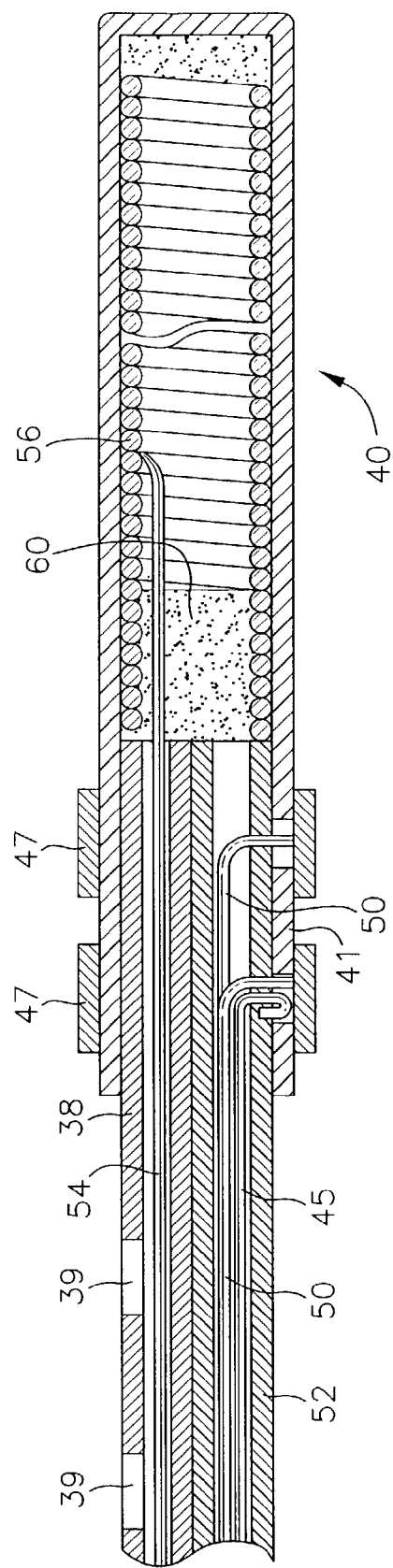

US 7,588,568 B2

ATRIAL ABLATION CATHETER AND METHOD FOR TREATING ATRIAL FIBRILLATION

FIELD OF THE INVENTION

The present invention relates to an improved steerable electrode catheter having an irrigated ablation electrode that is particularly useful for treating atrial fibrillation.

BACKGROUND OF THE INVENTION

Atrial fibrillation is a common sustained cardiac arrhythmia and a major cause of stroke. This condition is perpetuated by reentrant wavelets propagating in an abnormal atrial-tissue substrate. Various approaches have been developed to interrupt wavelets, including surgical or catheter-mediated atriotomy. It is believed that to treat atrial fibrillation by radiofrequency ablation using a catheter, continuous linear lesions must be formed to segment the heart tissue. By segmenting the heart tissue, no electrical activity can be transmitted from one segment to another. Preferably, the segments are made too small to be able to sustain the fibrillatory process. A preferred technique for treating atrial fibrillation by radiofrequency ablation would be a "branding iron" approach, where a relatively long electrode can be held stationary in good contact with the heart wall while ablation is completed. In this way, a continuous transmural burn may be effected.

U.S. Pat. No. 5,800,428 to Nelson et al. discloses a radio frequency ablation catheter system having a flexible, tubular electrode for creating a continuous linear lesion. The tubular electrode is selectively extendable from the distal end of the catheter. The catheter further comprises mechanisms for remotely manipulating and extending the electrode. However, having an extendable electrode house in the catheter provides less degrees of freedom with respect to the shape, size and length of the tubular electrode. Moreover, the physician has to deal with additional moving and manipulatable parts, adding complexity to the procedure. Further, a retractable electrode can cause contamination because blood or coagulate on the electrode can be pulled into and entrapped inside the catheter. The entrapped coagulate can also affect the ability of the electrode to be further extended and retracted. Accordingly, it would be desirable to provide a catheter design having an electrode for creating linear lesions that overcomes these drawbacks.

SUMMARY OF THE INVENTION

The invention is directed to an improved catheter for ablating tissue. The catheter comprises an elongated generally-tubular catheter body having proximal and distal ends and at least one lumen extending therethrough. A non-retractable ablation assembly is attached to the distal end of the catheter body. The ablation assembly comprises proximal and distal non-conductive tubings, each having a lumen extending therethrough, and a generally tubular electrode mounted between the proximal and distal non-conductive tubings. The tubular electrode is formed of a material having shape-memory and has at least one irrigation port through which fluid can pass from the inside to the outside of the electrode. The ablation assembly further comprises a non-conductive protective tubing extending generally parallel to and along the outside of the tubular electrode that has proximal and distal ends extending into the proximal and distal non-conductive tubings, respectively. The catheter further comprises at least one of an electrode lead wire and a temperature sensor wire, and preferably both, extending through the non-conductive protective tubing and catheter body. The electrode lead wire has a distal end mounted to a ring electrode mounted on the distal non-conductive tubing. The temperature sensor wire has a distal end mounted on or under the distal non-conductive tubing. The catheter also includes means for introducing fluid into the tubular electrode.

In another embodiment, the invention is directed to a catheter for ablating tissue comprising a catheter body having an outer wall, proximal and distal ends, and at least one lumen extending therethrough. An intermediate section comprising a segment of flexible tubing having proximal and distal ends and at least one lumen therethrough is fixedly attached at its proximal end to the distal end of the catheter body. A non-retractable ablation assembly as described above is attached to the distal end of the intermediate section. An infusion tube extends through a lumen in the intermediate section and has a distal end in fluid communication with the proximal end of the tubular electrode.

In another embodiment, the invention is directed to a method for treating atrial fibrillation. The method comprises inserting the distal end of a catheter as described above into an atria of the heart, and forming at least one linear lesion in the atrial tissue with the tubular electrode.

In yet another embodiment, the invention is directed to a method for treating atrial fibrillation comprising providing a catheter as described above and a guiding sheath having proximal and distal ends. The guiding sheath is inserted into the body so that the distal end of the guiding sheath is in an atria of the heart. The catheter is inserted into the proximal end of the guiding sheath and fed through the guiding sheath so that the distal end of the catheter extends out the distal end of the guiding sheath. The method further comprises forming at least one linear lesion in the atrial tissue with the tubular electrode.

DESCRIPTION OF THE DRAWINGS

These and other features and advantages of the present invention will be better understood by reference to the following detailed description when considered in conjunction with the accompanying drawings wherein:

FIG. 3B is a side cross-sectional view of the distal end of the tubular ablation assembly of FIG. 3A.

DETAILED DESCRIPTION

Figure 1:
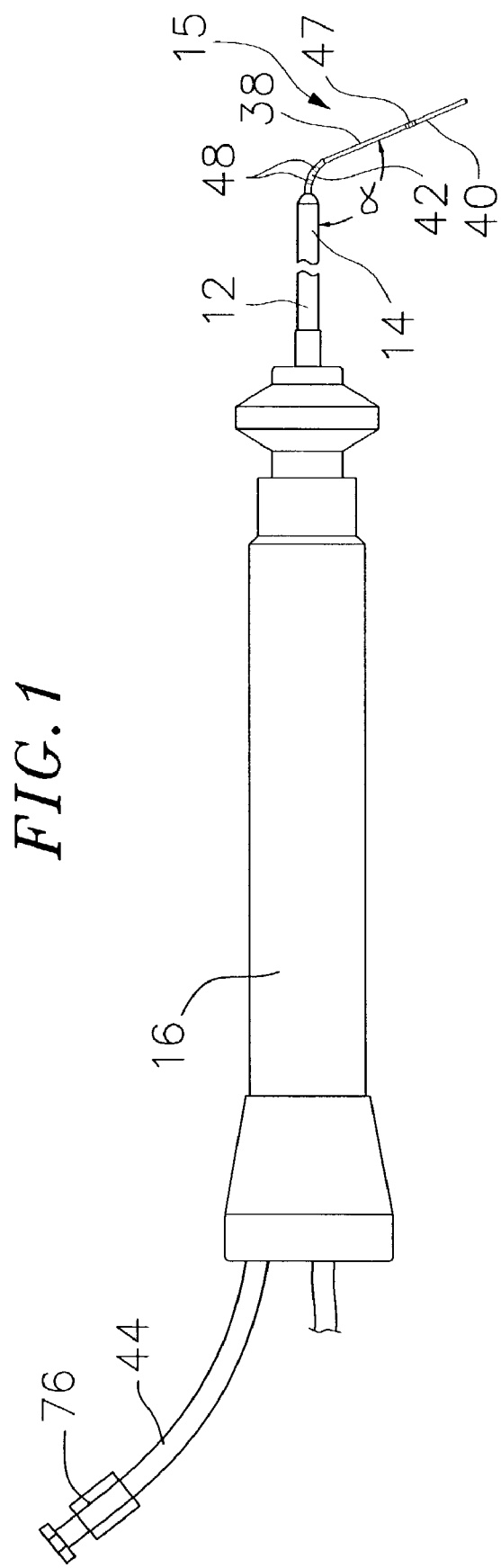
FIG. 1 is a side cross-sectional view of an embodiment of the catheter of the invention.

In a particularly preferred embodiment of the invention, there is provided a steerable catheter having an irrigated tubular ablation electrode. As shown in FIG. 1, catheter 10 comprises an elongated catheter body 12 having proximal and distal ends, an intermediate section 14 at the distal end of the catheter body, an ablation assembly 15 mounted at the distal end of the intermediate section, and a control handle 16 at the proximal end of the catheter body.

Figure 2:
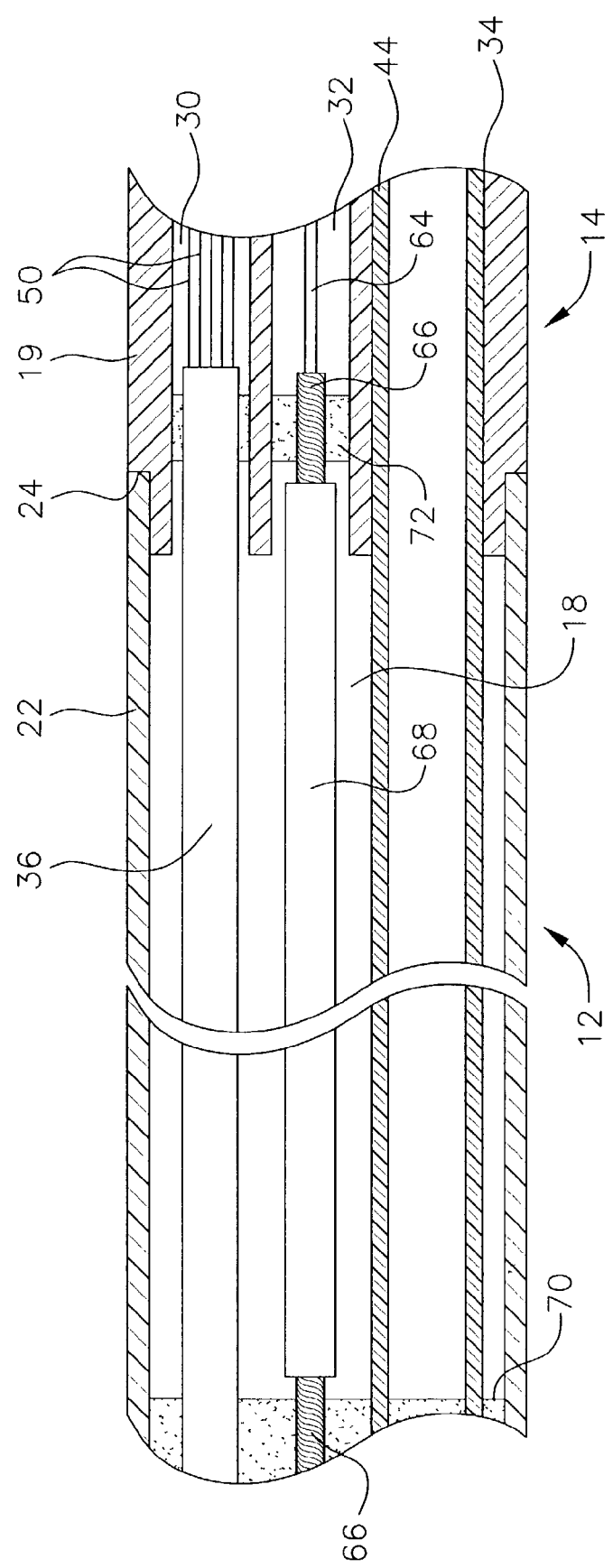
FIG. 2 is a side cross-sectional view of a catheter body according to the invention, including the junction between the catheter body and intermediate section.

With reference to FIG. 2, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A presently preferred construction comprises an outer wall 22 made of polyurethane or PEBAX. The outer wall 22 comprises an imbedded braided mesh of stainless steel or the like to increase torsional stiffness of the catheter body 12 so that, when the control handle 16 is rotated, the intermediate section 14 of the catheter 10 will rotate in a corresponding manner.

The outer diameter of the catheter body 12 is not critical, but is preferably no more than about 8 french, more preferably 7 french. Likewise the thickness of the outer wall 22 is not critical, but is thin enough so that the central lumen 18 can accommodate an infusion tube, a puller wire, lead wires, and any other wires, cables or tubes. If desired, the inner surface of the outer wall 22 is lined with a stiffening tube (not shown) to provide improved torsional stability. A particularly preferred catheter has an outer wall 22 with an outer diameter of from about 0.090 inch to about 0.94 inch and an inner diameter of from about 0.061 inch to about 0.065 inch.

In the depicted embodiment, the intermediate section 14 comprises a short section of tubing 19 having three lumens. The first lumen 30 electrode carries lead wires 50, the second lumen 32 carries a puller wire 64, and the third lumen 34 carries an infusion tube 44. The wires and tube are described in more detail below. The tubing 19 is made of a suitable non-toxic material that is preferably more flexible than the catheter body 12. A presently preferred material for the tubing 19 is braided polyurethane, i.e., polyurethane with an embedded mesh of braided stainless steel or the like, that is more flexible than the catheter body. The number and size of the lumens is not critical and can vary depending on the various wires, tubes and other components carried by the catheter. In a preferred embodiment, the intermediate section 14 has an outer diameter ranging from about 5 french (0.066 inch) to 8 french (0.105 inch), and the first lumen 30 and second lumen 32 are generally about the same size, each having a diameter of from about 0.020 inch to about 0.024 inch, preferably 0.022 inch, with the third lumen 34 having a slightly larger diameter of from about 0.032 inch to about 0.038 inch, preferably 0.035 inch.

A preferred means for attaching the catheter body 12 to the intermediate section 14 is illustrated in FIG. 2. The proximal end of the intermediate section 14 comprises an outer circumferential notch 24 that receives the inner surface of the outer wall 22 of the catheter body 12. The intermediate section 14 and catheter body 12 are attached by glue or the like.

If desired, a spacer (not shown) can be located within the catheter body at its distal end, adjacent the proximal end of the intermediate section. The spacer provides a transition in flexibility at the junction of the catheter body and intermediate section, which allows this junction to bend smoothly without folding or kinking. A catheter having such a spacer is described in U.S. Pat. No. 5,964,757, the disclosure of which is incorporated herein by reference.

At the distal end of the intermediate section 14 is a non-retractable ablation assembly 15, as shown in FIGS. 1, 3A, 3B and 4. In the depicted embodiment, the ablation assembly 15 has proximal and distal ends and comprises a tubular electrode 38 between a non-conductive distal segment 40 and a non-conductive proximal segment 42, all described further below.

The ablation assembly 15 is shaped so that it is bent relative to the straight tubing 19 of the intermediate section 14. As used herein, the term "bent" when used to describe the ablation assembly 15 is intended to mean that the assembly is curved, bent or angled to any extent at any point along its length. With this design, when a physician deflects the intermediate section 14, the tubular electrode 38 is pressed against the tissue, creating a "branding iron" effect. In contrast, a physician using a straight catheter having one or more electrodes along the length of its distal end to create a linear lesion will find it difficult to provide the same amount of pressure on the tissue with the electrode(s). The particular shape of the ablation assembly 15 depends on the desired application, i.e., the precise location in the atrium or elsewhere at which the catheter is to be used, and for example, can be bent in a single plane or in multiple planes.

In one embodiment, as shown in FIG. 1, the tubular ablation assembly 15 is generally L-shaped and lies in a single plane. The proximal end of the assembly 15 is generally straight and collinear with the tubing 19 of the intermediate section 14. The assembly 15 bends at a point along its length. Preferably the straight proximal end of the assembly 15 is sufficiently long to mount one or more mapping ring electrodes, as described in more detail below. After the bend, the distal end of the assembly 15 is generally straight. The exposed portion of the tubular electrode 38, i.e., the portion that is not covered by any non-conductive tubing, is generally L-shaped, but alternatively could be generally straight or one of a variety of other shapes, such as that described below. The non-conductive distal segment 40 is generally collinear with the distal end of the tubular electrode 38. The ablation assembly 15 of this embodiment is preferably shaped so that it forms an angle $\alpha$ ranging from about 60 degrees to about 140 degrees. This design is particularly useful for ablation in the open region of the heart.

Figure 5:
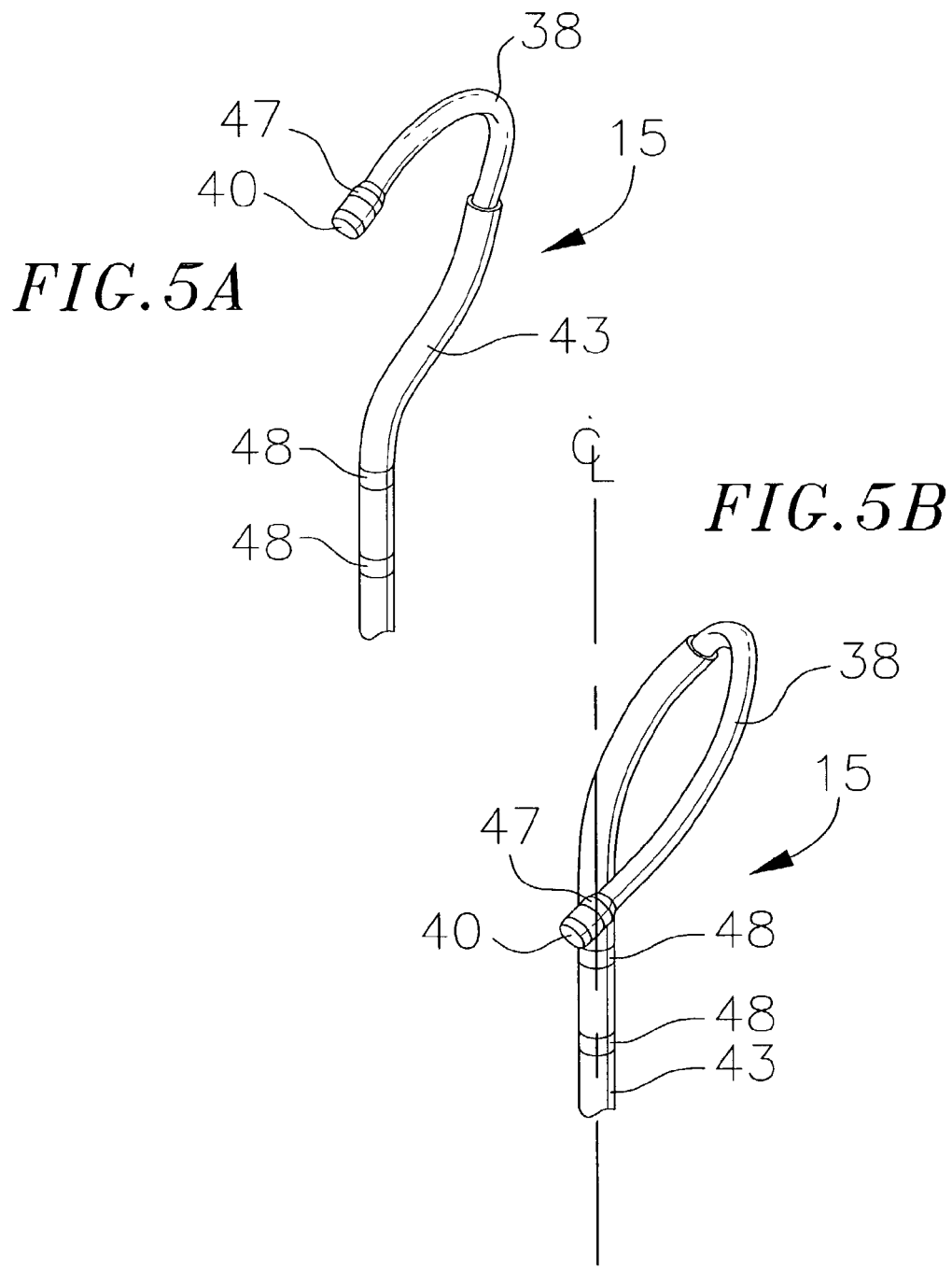
FIGS. 5A and 5B are perspective views of an alternate tubular ablation assembly according to the invention.

In an alternative embodiment, shown in FIGS. 5A and 5B, the ablation assembly 15 is generally lasso-shaped. The proximal end of the assembly 15 is generally collinear with the tubing 19 of the intermediate section 14. The assembly 15 curves at its distal end to form a slanted semi-circle, i.e., lying in more than one plane, as best shown in FIG. 5B. In this embodiment, the tubular electrode 38 is generally curved. This design is particularly useful for ablation in or around a blood vessel, such as the pulmonary vein. As would be recognized by one skilled in the art, other shapes can be provided for the electrode assembly 15. For example, in the embodiment of FIG. 5B, the tubular electrode 38 forms a full circle.

As used herein, the term "tubular electrode" refers not only to traditional tubular, i.e., cylindrically-shaped, structures having a hollow interior, but also to any other elongated, generally-hollow bodies having, for example, an ovular, square, or other geometrically-shaped cross-sectional. Other shapes will be apparent to those skilled in the art to achieve the purpose described further herein. Preferably the tubular electrode 38 has an inner diameter ranging from about 0.018 inch to about 0.024 inch and an outer diameter ranging from about 0.020 inch to about 0.028 inch. The length of the exposed portion of the tubular electrode 38 can vary depending on the desired length of the lesion to be created, and preferably ranges from about 8 mm to about 2 cm, more preferably from about 1.2 cm to about 1.6 cm, to create a relatively long lesion.

The tubular electrode 38 is made of a material having shape-memory, i.e., that can be straightened or bent out of its original shape upon exertion of a force and is capable of substantially returning to its original shape upon removal of the force. A particularly preferred material for the tubular electrode is a nickel/titanium alloy. Such alloys typically comprise about 55% nickel and 45% titanium, but may comprise from about 54% to about 57% nickel with the balance being titanium. A preferred nickel/titanium alloy is nitinol, which has excellent shape memory, together with ductility, strength, corrosion resistance, electrical resistivity and temperature stability. A particularly preferred material is nitinol form from 50.8 atomic % nickel, with the balance titanium, having an austenite finish and a transition temperature from about +5° C. to about −25° C., which is commercially available from Nitinol Device Corp. (Fremont, Calif.).

The tubular electrode 38 contains a series of irrigation ports 39 through which fluid can pass during an ablation procedure. Preferably the irrigation ports 39 are located only on the side of the tubular electrode 38 that is to be in contact with the tissue to be ablated. The irrigation ports 39 can be any suitable shape, such as rectangular or ovular slots or round holes. In the embodiment shown in FIGS. 1, 3 and 4, the tubular electrode 38 has six irrigation ports 39, each forming a slot or ellipse with a length preferably ranging from about 0.018 inch to about 0.020 inch. Preferably the irrigation ports 39 are spaced apart from each other a distance of about 0.125 inch. Having a limited number of irrigation ports 39 on the side of the tubular electrode 38 in contact with the tissue to be ablated allows for more even fluid flow out of the electrode. As would be recognized by one skilled in the art, the precise number, size, shape and arrangement of irrigation ports 39 can vary as desired.

An electrode lead wire 50 is attached to the tubular electrode 38 for electrical connection to a suitable connector (not shown), which is attached to a source of RF energy (not shown). In the depicted embodiment, the electrode lead wire 50 is wrapped around the proximal end of the tubular electrode 38 and soldered, welded or otherwise attached to the electrode. The electrode lead wire 50 for the tubular electrode 38 extends through the first lumen 30 of the intermediate section 14, through the central lumen 18 of the catheter body 12, and through the control handle 16, and are connected to a suitable source of ablation energy (not shown) by means of an appropriate connector as is generally known in the art.

The distal and proximal non-conductive segments 40 and 42 of the ablation assembly 15 comprise distal and proximal non-conductive coverings 41 and 43, respectively, which are preferably made of polyimide or other biocompatible plastic. The distal non-conductive covering 41 extends over the distal end of the tubular electrode 38, and the proximal non-conductive covering 43 extends over the proximal end of the tubular electrode.

In the depicted embodiment, two distal ring electrodes 47 are mounted on the distal non-conductive covering 41, and two proximal ring electrodes 48 are mounted on the proximal non-conductive covering 43. The ring electrodes 47 and 48 can be made of any suitable material, and are preferably made of platinum or platinum and iridium. Each ring electrode can be mounted by any suitable technique, and is preferably mounted by first forming a hole in the non-conductive covering. An electrode lead wire 50 is fed through the hole, and the ring electrode is welded in place over the lead wire and non-conductive covering. The presence and number of ring electrodes can vary as desired.

Figure 3A:
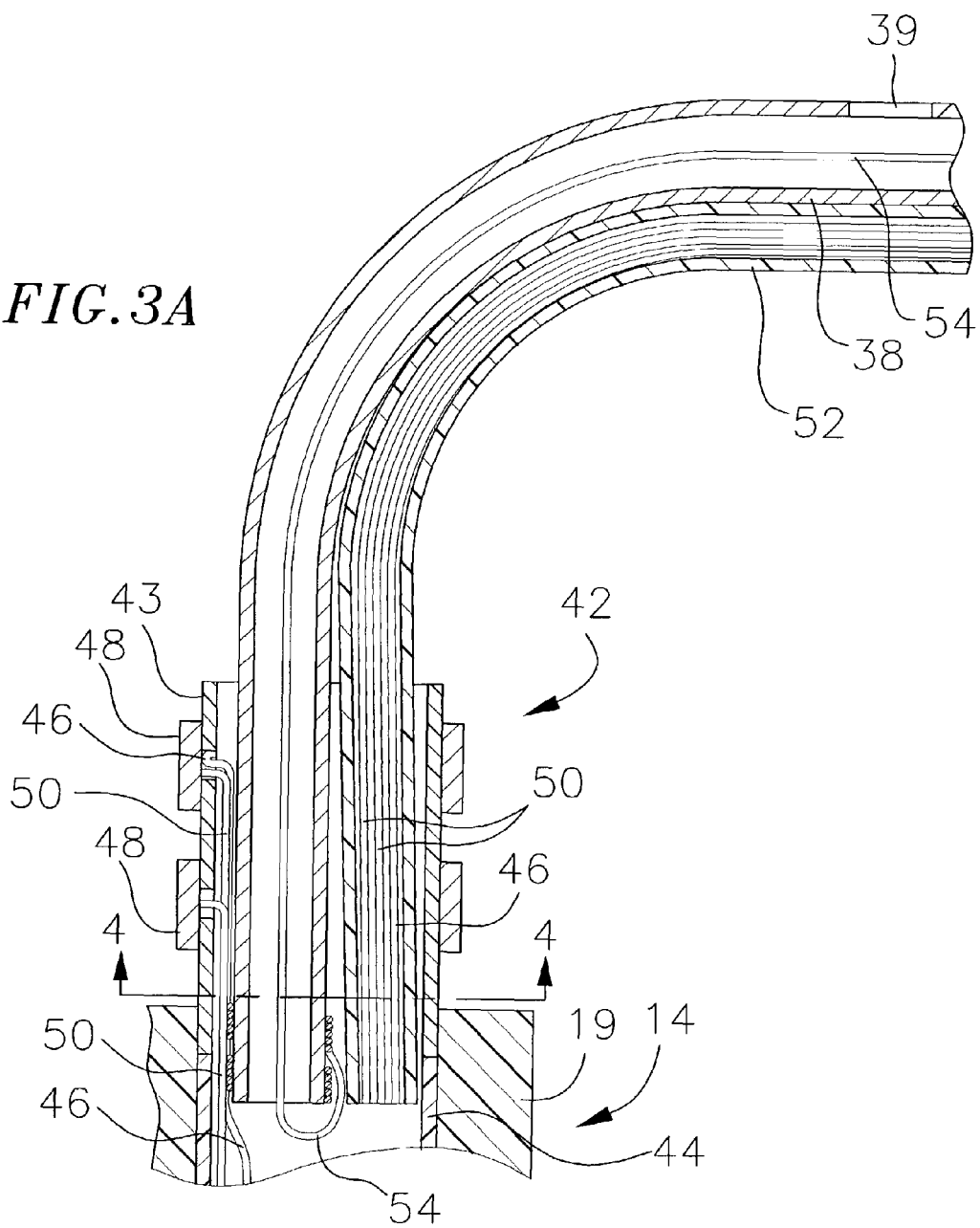
FIG. 3A is a side cross-sectional view of the proximal end of a tubular ablation assembly according to the invention.
Figure 4:
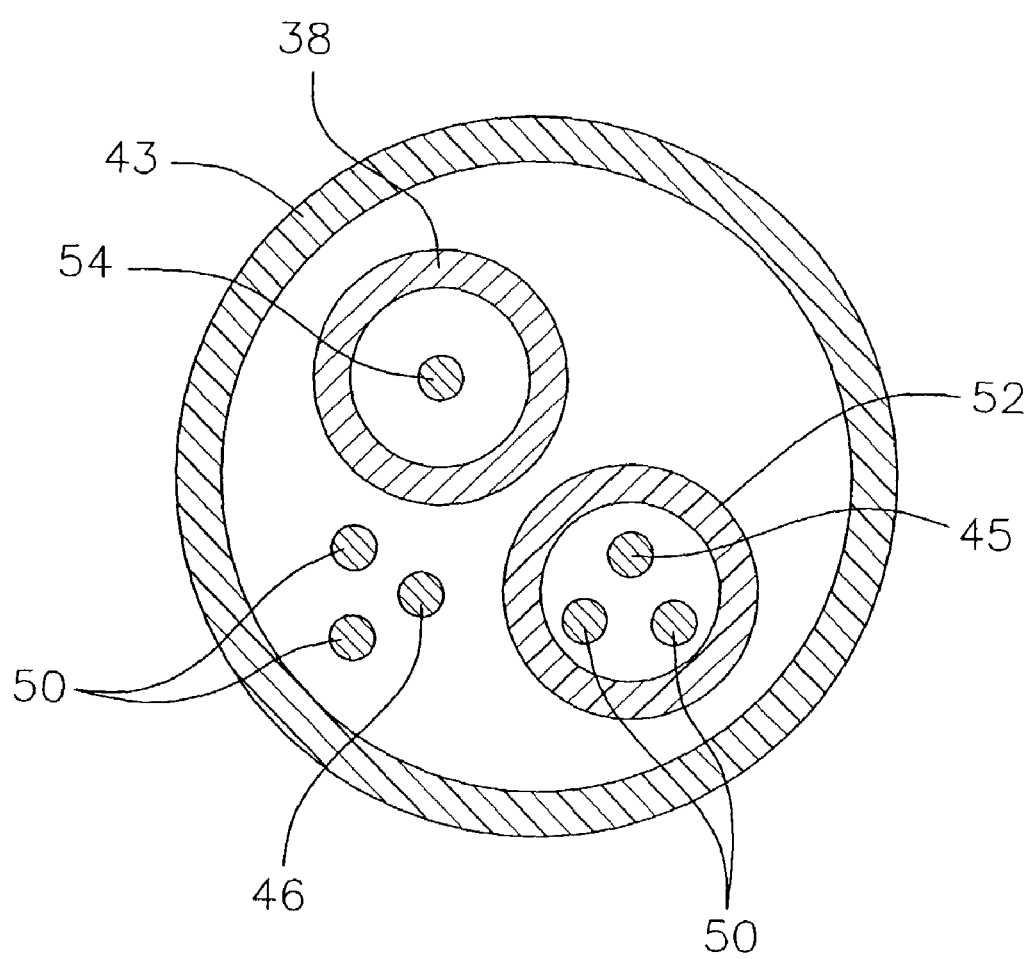
FIG. 4 is an end cross-sectional view of the tubular ablation assembly of FIG. 3A along line 4-4.

Additionally, one or more temperature sensing means are provided for the tubular electrode 38. Any conventional temperature sensing means, e.g., a thermocouple or thermistor, may be used. In the depicted embodiment, two thermocouples are provided, each of which is formed by a wire pair. One wire of the wire pair is a copper wire, e.g., a number 38 copper wire, and the other wire of the wire pair is a constantan wire, which gives support and strength to the wire pair. Specifically, a distal thermocouple 45 is provided for measurement distal to the exposed portion of the tubular electrode 38, and a proximal thermocouple 46 is provided for measurement proximal to the exposed portion of the tubular electrode. Each thermocouple 45 and 46 is preferably mounted to a corresponding ring electrode 47 and 48, as shown in FIGS. 3A and 3B, by weld, solder or other suitable method. The placement of the thermocouples in the depicted embodiment is particularly desirable because they are located out of the irrigation zone, i.e., the region in which the irrigation fluid primarily flows from the tubular electrode 38 through the irrigation ports 39. The presence of the fluid can reduce the accuracy of the tissue temperature measurements by the thermocouples. Accordingly, it is desirable to place the thermocouples or other temperature sensing means as close as possible to the tubular electrode 38 while outside the irrigation zone.

In the depicted embodiment, a non-conductive protective sheath 52 is provided along the outside of the tubular electrode 38 for carrying the distal thermocouple wires 45 and electrode lead wires 50 connected to the distal ring electrodes 47. The protective sheath 52 extends generally parallel to the tubular electrode 38 and is preferably attached to the tubular electrode along the entire exposed portion of the tubular electrode. The protective sheath 52 is preferably made of polyurethane or polyimide or other suitable biocompatible plastic. In a preferred embodiment, the protective sheath 52 is glued to the tubular electrode 38 with an adhesive such as Krazy Glue® and tied in place using a monofilament or the like. The tubular electrode 38 and protective sheath 52 are then covered with a polyurethane glue or the like, with care being taken not to cover the irrigation ports 38, and the monofilament is removed after the polyurethane glue cures. The proximal and distal ends of the protective sheath 52 extend into the proximal and distal non-conductive coverings 43 and 41. Alternatively, the distal electrode lead wires 50 and distal thermocouple wires 45 can extend through the tubular electrode 38, although such wires can adversely affect the flow of irrigation fluid through the tubular electrode.

All of the electrode lead wires 50 and thermocouple wires 45 and 46 extend through the first lumen 30 in the intermediate section 14. Within the catheter body 12, the wires 45, 46 and 50 extend through a protective tubing 36 to keep the wires from contacting other components extending through the central lumen 18. The protective tubing 36 is preferably anchored at its distal end to the proximal end of the intermediate section 14 by gluing it in the first lumen 30 with polyurethane glue or the like. The electrode lead wires 50 then extend out through the control handle 16 and to a suitable monitoring device or source of ablation energy (not shown), as appropriate, via a suitable connector (now shown), as is generally known in the art. The thermocouple wires 45 and 46 similarly extend out through the control handle 16 and to a connector (not shown) connectable to a temperature monitor (not shown).

The distal end of the ablation assembly 15 is preferably provided with an atraumatic construction to prevent the distal end of the tubular electrode 38 from penetrating tissue. In the depicted embodiment, the atraumatic construction comprises a tightly wound coil spring 56 made, for example, of stainless steel, such as the mini guidewire commercially available from Cordis Corporation (Miami, Fla.). The coil spring 56 is mounted within the distal end of the distal non-conductive covering 41 and held in place at its proximal and distal ends with polyurethane glue 60 or the like. In the depicted embodiment, the coil spring 56 has a length of about 0.50 inch, but can be any desired length, for example, ranging from about 0.25 inch to about 1.0 inch. The coil spring 56 is preferably sufficiently long to serve as an anchor for introducing the catheter into a guiding sheath, particularly when the tubular electrode is curved and must be straightened upon introduction into the sheath. Without having the coil spring 56 as an anchor, the tubular electrode 38 has a tendency to pull out of the guiding sheath upon its introduction into the guiding sheath. Additionally, if desired, the coil spring 56 can be formed, at least in part, of a radiopaque material to aid in the positioning of the tubular electrode 38 under fluoroscopy.

The coil spring 56 is preferably secured to the distal end of the catheter with a safety wire 54. The distal end of the safety wire 54 is hooked around the coil spring 56 and glued in place. The safety wire 54 extends through the tubular electrode 38 and its proximal end is wrapped around the proximal end of the tubular electrode and optionally soldered, glued or otherwise attached in place. The proximal end of the safety wire 54 can be secured to the catheter in any other suitable manner. For example, in an alternative embodiment, (not shown) the safety wire can extend through the protective sheath 42 and through the catheter body 12 and be anchored within the control handle 16.

Figure 6:
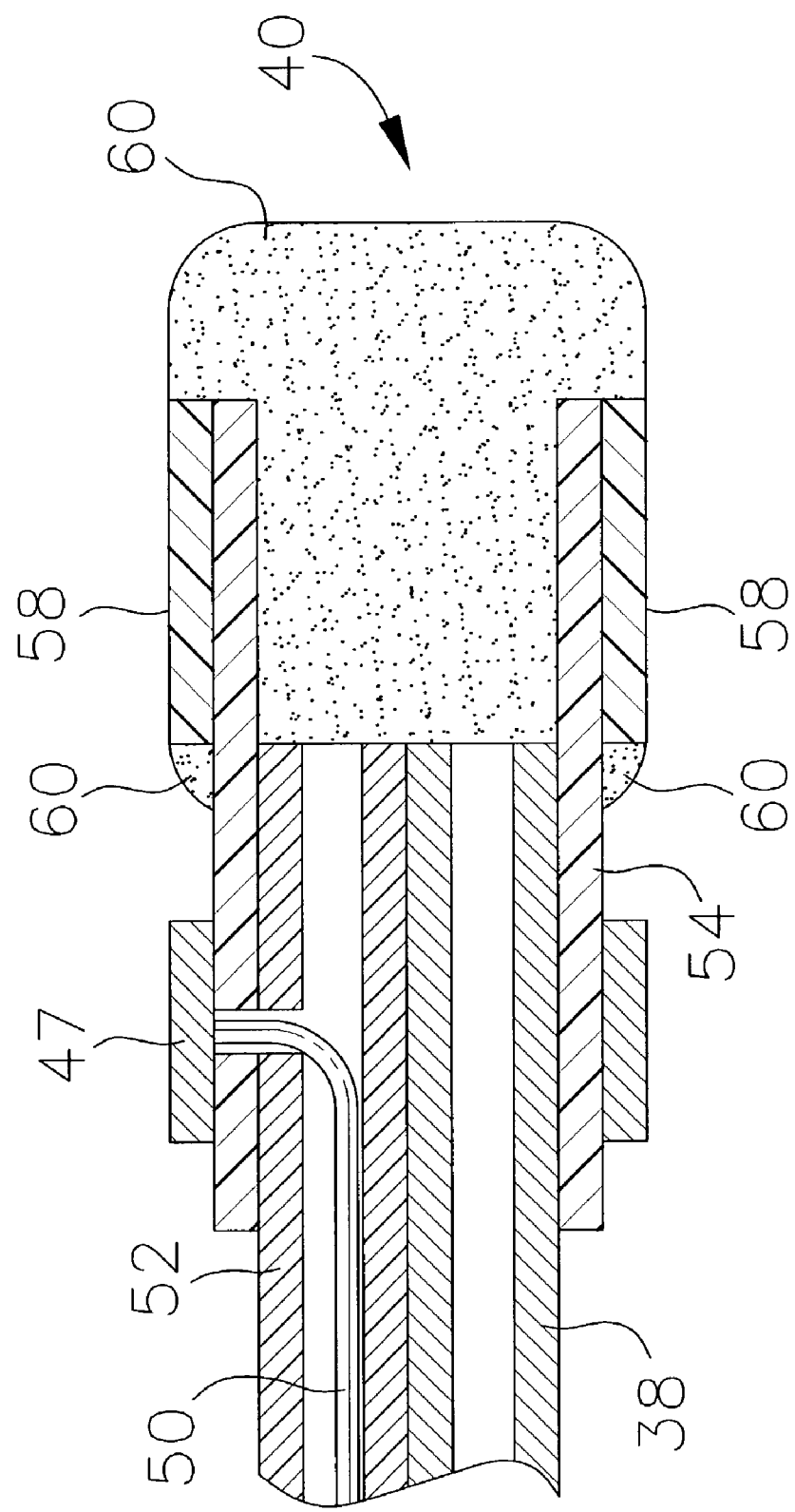
FIG. 6 is a side cross-sectional view of the distal end of an alternate tubular ablation assembly according to the invention.

The distal non-conductive segment 40 can have any other suitable atraumatic construction that protects the tubular electrode 38 from puncturing the heart tissue. An example of an alternative atraumatic construction, as shown in FIG. 6, is in the form of a ball. To form the ball, the distal end of the distal non-conductive covering 41 is covered with a short length of thick non-conductive tubing 58, made of polyimide, polyurethane or the like. Polyurethane adhesive 60 or the like is applied into and around the edges of the non-conductive tubing 58 to round off the edges of the distal end of the distal non-conductive segment 40.

A puller wire 64 is provided for deflection of the intermediate section 14. The puller wire 64 extends through the catheter body 12, is anchored at its proximal end to the control handle 16, and is anchored at its distal end to the intermediate section 14. The puller wire 64 is made of any suitable metal, such as stainless steel or Nitinol, and is preferably coated with Teflon® or the like. The coating imparts lubricity to the puller wire 64. The puller wire 64 preferably has a diameter ranging from about 0.006 to about 0.010 inch.

A compression coil 66 is situated within the catheter body 12 in surrounding relation to the puller wire 64. The compression coil 66 extends from the proximal end of the catheter body 12 to the proximal end of the intermediate section 14. The compression coil 66 is made of any suitable metal, preferably stainless steel. The compression coil 66 is tightly wound on itself to provide flexibility, i.e., bending, but to resist compression. The inner diameter of the compression coil 66 is preferably slightly larger than the diameter of the puller wire 64. The Teflon® coating on the puller wire 64 allows it to slide freely within the compression coil 66. If desired, particularly if the lead wires 50 are not enclosed by a protective tubing 36, the outer surface of the compression coil 66 is covered by a flexible, non-conductive sheath 68, e.g., made of polyimide tubing, to prevent contact between the compression coil and any other wires within the catheter body 12.

The compression coil 66 is anchored at its proximal end to the outer wall 22 of the catheter body 12 by proximal glue joint 70 and at its distal end to the intermediate section 14 by distal glue joint 72. Both glue joints 70 and 72 preferably comprise polyurethane glue or the like. The glue may be applied by means of a syringe or the like through a hole made between the outer surface of the catheter body 12 and the central lumen 18. Such a hole may be formed, for example, by a needle or the like that punctures the outer wall 22 of the catheter body 12 which is heated sufficiently to form a permanent hole. The glue is then introduced through the hole to the outer surface of the compression coil 66 and wicks around the outer circumference to form a glue joint about the entire circumference of the compression coil 66.

Figure 7:
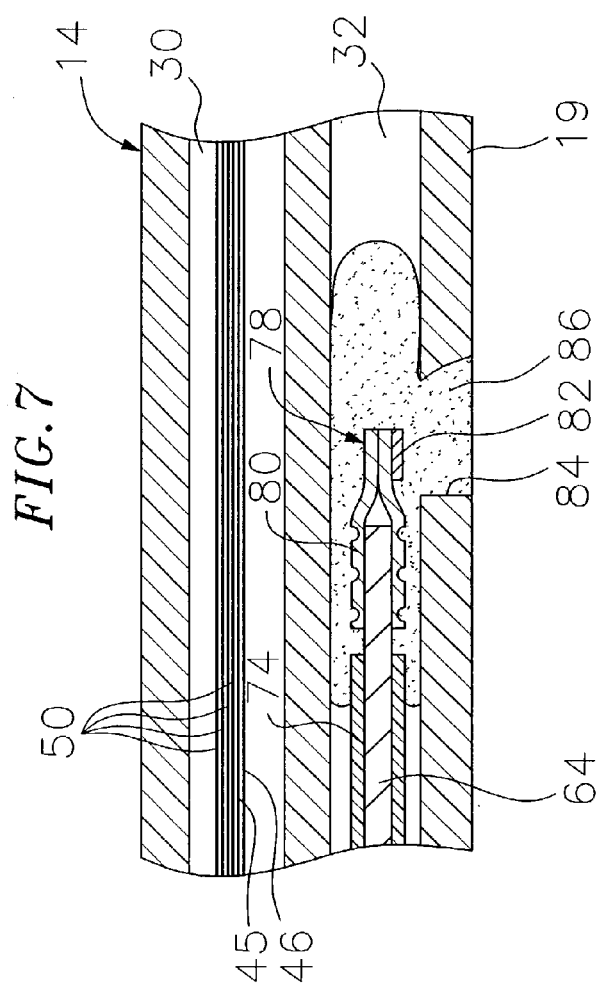
FIG. 7 is a cross sectional view of a portion of the catheter intermediate section showing one means for attaching the puller wire.
Figure 9:
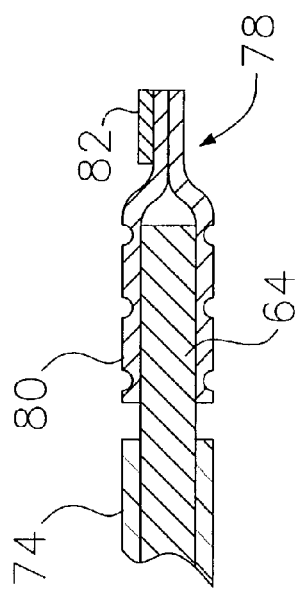
FIG. 9 is a side cross sectional views of the puller wire anchor of FIG. 8.
Figure 8:
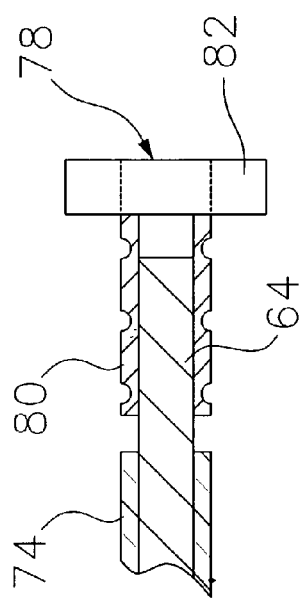
FIG. 8 is a top cross sectional views of a preferred puller wire anchor.

The puller wire 64 extends into the second lumen 32 of the intermediate section 14. Preferably the puller wire 64 is anchored at its distal end to the side of the intermediate section 14, as shown in FIGS. 7 to 9. A T-shaped anchor 78 is formed which comprises a short piece of tubular stainless steel 80, e.g., hypodermic stock, which is fitted over the distal end of the puller wire 64 and crimped to fixedly secure it to the puller wire. The distal end of the tubular stainless steel 80 is fixedly attached, e.g., by welding, to a stainless steel crosspiece 82 such as stainless steel ribbon or the like. The crosspiece 82 sits in a notch 84 in a wall of the flexible tubing 19 that extends into the second lumen 32 of the intermediate section 14. The stainless steel cross-piece 82 is larger than the opening and, therefore, cannot be pulled through the opening. The portion of the notch 84 not filled by the cross-piece 82 is filled with glue 86 or the like, preferably a polyurethane glue, which is harder than the material of the flexible tubing 19. Rough edges, if any, of the cross-piece 82 are polished to provide a smooth, continuous surface with the outer surface of the flexible tubing 19. Within the second lumen 32 of the intermediate section 14, the puller wire 64 extends through a plastic, preferably Teflon®, puller wire sheath 74, which prevents the puller wire 64 from cutting into the wall of the intermediate section 14 when the intermediate section is deflected. Any other suitable technique for anchoring the puller wire 64 in the intermediate section 14 can also be used.

Longitudinal movement of the puller wire 42 relative to the catheter body 12, which results in deflection of the intermediate section 14, is accomplished by suitable manipulation of the control handle 16. Examples of suitable control handles for use in the present invention are disclosed, for example, in U.S. Pat. Nos. Re 34,502 and 5,897,529, the entire disclosures of which are incorporated herein by reference.

Within the third lumen 34 of the intermediate section 14 is provided an infusion tube 44 for infusing fluids, e.g., saline, to cool the tubular electrode 38 and surrounding tissue during ablation. The infusion tube 44 extends through the third lumen 34 of the intermediate section 14, through the catheter body 12, out the proximal end of the control handle 16, and terminates in a luer hub 76 or the like at a location proximal to the control handle. In an alternative arrangement, a single lumen side arm (not shown) is fluidly connected to the central lumen 18 near the proximal end of the catheter body 12, as described in more detail in U.S. Pat. No. 6,120,476, the entire disclosure of which is incorporated herein by reference. Alternatively, the infusion tube 44 can terminate within the distal end of the third lumen 34 of the intermediate section 14, with a second infusion tube provided that extends from the proximal end of the third lumen, through the catheter body 12 and out through the control handle 16. Such a design is also described in more detail in U.S. Pat. No. 6,120,476. As shown in FIG. 3, the distal end of the infusion tube 44 extends over the proximal end of the tubular electrode 38, including the lead wire 50 and safety wire 54 wrapped around the tubular electrode. The infusion tube 44 is attached to the tubular electrode 38 with polyurethane glue or the like, which also acts to seal the third lumen 34 so that fluids cannot pass into or out of the third lumen other than through the infusion tube and tubular electrode.

In use, a suitable guiding sheath is inserted into the patient. An example of a suitable guiding sheath for use in connection with the present invention is the Preface™ Braiding Guiding Sheath, commercially available from Cordis Webster (Diamond Bar, Calif.). The distal end of the sheath is guided into one of the atria. A catheter in accordance with the present invention is fed through the guiding sheath until its distal end extends out of the distal end of the guiding sheath. As the catheter is fed through the guiding sheath, the tubular electrode 38 can be straightened to fit through the sheath, and it will return to its original shape upon removal of the sheath.

The tubular electrode 38 is then used to form continuous linear lesions by ablation. As used herein, a linear lesion refers to any lesion, whether curved or straight, between two anatomical structures in the heart that is sufficient to block a wavelet, i.e., forms a boundary for the wavelet. Anatomical structures, referred to as "atrial trigger spots", are those regions in the heart having limited or no electrical conductivity and are described in Haissaguerre et al., "Spontaneous Initiation of Atrial Fibrillation by Ectopic Beats Originating in the Pulmonary Veins", New England Journal of Medicine, 339:659-666 (Sep. 3, 1998), the disclosure of which is incorporated herein by reference. The linear lesions typically have a length of from about 1 cm to about 4 cm, but can be longer or shorter as necessary for a particular procedure. The thermocouples or other temperature sensing means can be used to monitor the temperature of the tissue during ablation.

Figure 10:
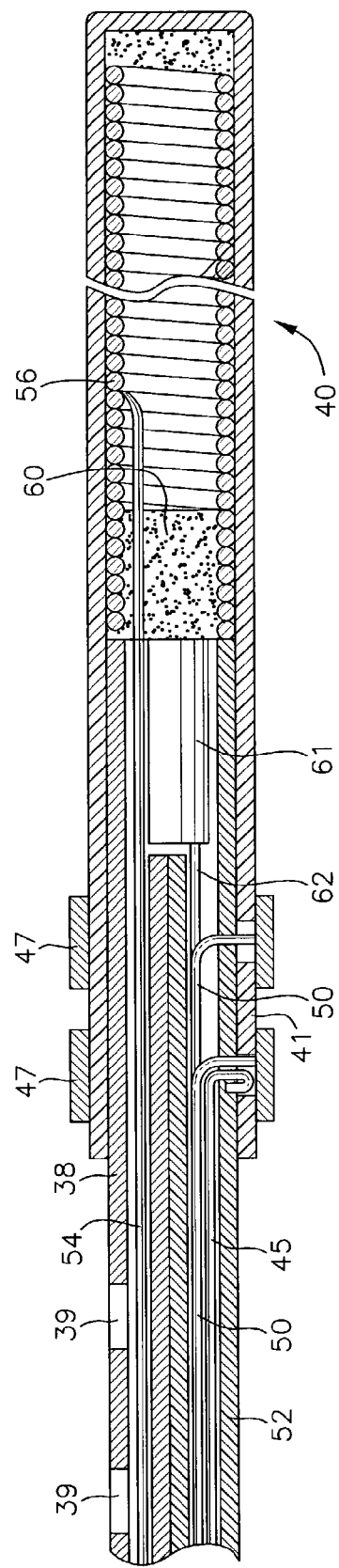
FIG. 10 is a side cross-sectional view of the distal end of the tubular ablation assembly of an alternative embodiment including a location sensor.

In an alternative embodiment, as shown in FIG. 10, the ablation assembly 15 further includes a location sensor 61 for providing location information about the ablation assembly. Preferably the location sensor 61 comprises a magnetic-field-responsive coil, as described in U.S. Pat. No. 5,391,199, or a plurality of such coils, as described in International Publication WO 96/05758. The plurality of coils enables six-dimensional position and orientation coordinates to be determined. Alternatively, any suitable position sensor known in the art may be used, such as electrical, magnetic or acoustic sensors. Suitable location sensors for use with the present invention are also described, for example, in U.S. Pat. Nos. 5,558,091, 5,443,489, 5,480,422, 5,546,951, and 5,568,809, and International Publication Nos. WO 95/02995, WO 97/24983, and WO 98/29033, the disclosures of which are incorporated herein by reference.

In the depicted embodiment, the location sensor 61 is mounted in the non-conductive distal segment 40 within the distal non-conductive covering 41, distal to the distal end of the tubular electrode 38 and proximal to the proximal end of the coil spring 56. In accordance with the invention, the location sensor 61 could be mounted at other positions within the ablation assembly 15 depending on the precise position on the assembly to be located during a procedure. The location sensor 56 is connected to a sensor cable 62 that extends through the protective sheath 52, the catheter body 12 and control handle 16 and out the proximal end of the control handle within an umbilical cord (not shown) to a sensor control module (not shown) that houses a circuit board (not shown). Alternatively, the circuit board can be housed within the control handle 16, for example, as described in U.S. Pat. No. 6,024,739, the disclosure of which is incorporated herein by reference. The sensor cable 62 comprises multiple wires encased within a plastic covered sheath. In the sensor control module, the wires of the sensor cable are connected to the circuit board. The circuit board amplifies the signal received from the corresponding location sensor and transmits it to a computer in a form understandable by the computer by means of the sensor connector at the proximal end of the sensor control module. Also, because the catheter is designed for single use only, the circuit board preferably contains an EPROM chip that shuts down the circuit board approximately twenty-four hours after the catheter has been used. This prevents the catheter, or at least the location sensor, from being used twice.

If desired, two or more puller wires can be provided to enhance the ability to manipulate the intermediate section. In such an embodiment, a second puller wire and a surrounding second compression coil extend through the catheter body and into an additional off-axis lumen in the intermediate section. The first puller wire is preferably anchored proximal to the anchor location of the second puller wire. Suitable designs of catheters having two or more puller wires, including suitable control handles for such embodiments, are described, for example, in U.S. Pat. Nos. 6,123,699, 6,171,277, 6,183,435, 6,183,463, 6,198,974, 6,210,407, and 6,267,746, the disclosures of which are incorporated herein by reference.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

The invention claimed is:

1. A catheter for ablating tissue, the catheter comprising:
an elongated generally-tubular catheter body having proximal and distal ends and at least one lumen extending therethrough;
a non-retractable ablation assembly attached to the distal end of the catheter body, wherein the ablation assembly is fixedly bent relative to the catheter body, the ablation assembly comprising:
proximal and distal non-conductive tubings, each having a lumen extending therethrough, the distal non-conductive segment comprising a coil spring,
a single, continuous generally tubular elongated electrode mounted between the proximal and distal non-conductive tubings, the tubular electrode having a proximal end attached to the proximal non-conductive tubing and a distal end attached to the distal non-conductive tubing, the tubular electrode being formed of a material having shape-memory having at least one irrigation port through which fluid can pass from the inside to the outside of the electrode, wherein the tubular electrode has an elongated exposed portion extending between the proximal and distal non-conductive tubings, the exposed portion adapted to contact said tissue to provide a continuous linear lesion, and a non-conductive protective tubing extending generally parallel to and along the outside of the tubular electrode and having proximal and distal ends extending into the proximal and distal non-conductive tubings, respectively;

at least one of an electrode lead wire and a temperature sensor wire extending through the non-conductive protective tubing and catheter body, the electrode lead wire having a distal end mounted to a ring electrode mounted on the distal non-conductive tubing, and the temperature sensor wire having a distal end mounted on or under the distal non-conductive tubing; and means for introducing fluid into the tubular electrode.

2. The catheter according to claim 1, further comprising an intermediate section comprising a segment of flexible tubing having proximal and distal ends and at least one lumen therethrough, wherein the proximal end of the intermediate section is fixedly attached to the distal end of the catheter body and the proximal end of the ablation assembly is fixedly attached to the distal end of the intermediate section.

3. The catheter of claim 2, wherein the segment of flexible tubing of the intermediate section is more flexible than the catheter body.

4. A catheter according to claim 1, wherein the introducing means comprises an infusion tube extending through the catheter body and having proximal and distal ends, wherein the distal end of the infusion tube is in fluid communication with the proximal end of the tubular electrode.

5. A catheter according to claim 1, wherein the ablation assembly forms an angle α ranging from about 60° to 140° relative to the catheter body.

6. A catheter for ablating tissue, the catheter comprising:
a catheter body having an outer wall, proximal and distal ends, and at least one lumen extending therethrough;
an intermediate section comprising a segment of flexible tubing having proximal and distal ends and at least one lumen therethrough, the proximal end of the intermediate section being fixedly attached to the distal end of the catheter body;
a non-retractable ablation assembly attached to the distal end of the intermediate section, wherein the ablation assembly is fixedly bent relative to the intermediate section, the ablation assembly comprising;
proximal and distal non-conductive tubings, each having a lumen extending therethrough, the distal non-conductive tubing comprising a coil spring,
a single, continuous generally tubular elongated electrode mounted between the proximal and distal non-conductive tubings, the tubular electrode having a proximal end attached to the proximal non-conductive tubing and a distal end attached to the distal non-conductive tubing, the tubular electrode being formed of a material having shape-memory having at least one irrigation port through which fluid can pass from the inside to the outside of the electrode, wherein the tubular electrode has an elongated exposed portion extending between the proximal and distal non-conductive tubings, the exposed portion adapted to contact said tissue to provide a continuous linear lesion, and
a non-conductive protective tubing extending generally parallel to and along the outside of the tubular electrode and having proximal and distal ends extending into the proximal and distal non-conductive tubings, respectively;
at least one of an electrode lead wire and a temperature sensor wire extending through the non-conductive protective tubing and catheter body, the electrode lead wire having a distal end mounted to a ring electrode mounted on the distal non-conductive tubing, and the temperature sensor wire having a distal end mounted on or under the distal non-conductive tubing; and
an infusion tube extending through a lumen in the intermediate section and having proximal and distal ends, wherein the distal end of the infusion tube is in fluid communication with the proximal end of the tubular electrode.

7. A catheter according to claim 6, wherein the ablation assembly is generally L-shaped.

8. A catheter according to claim 6, wherein the ablation assembly is generally lasso-shaped.

9. A catheter according to claim 6, wherein the tubular electrode is made of a nickel/titanium alloy.

10. A catheter according to claim 6, wherein the tubular electrode is made of nitinol.

11. A catheter according to claim 6, wherein the exposed portion of the tubular electrode has a length ranging from about 8 mm to about 2 cm.

12. A catheter according to claim 6, wherein the ablation assembly comprises at least one electrode mounted on the distal non-conductive tubing.

13. A catheter according to claim 6, wherein the ablation assembly comprises at least one electrode on the proximal non-conductive tubing.

14. A catheter according to claim 6, wherein the ablation assembly comprises at least one electrode mounted on the distal non-conductive tubing and at least one electrode mounted on the proximal non-conductive tubing.

15. A catheter according to claim 14, wherein the ablation assembly comprises at least one temperature sensor mounted proximal to the exposed portion of the tubular electrode and at least one temperature sensor mounted distal to the exposed portion of the tubular electrode.

16. A catheter according to claim 6, wherein the ablation assembly comprises at least one temperature sensor mounted proximal or distal to the exposed portion of the tubular electrode.

17. A catheter according to claim 6, wherein the ablation assembly comprises at least one temperature sensor mounted proximal to the exposed portion of the tubular electrode and at least one temperature sensor mounted distal to the exposed portion of the tubular electrode.

18. A catheter according to claim 6, wherein the at least one irrigation port is located only on the side of the tubular electrode that is to be in contact with the tissue to be ablated.

19. A catheter according to claim 6, further comprising a control handle mounted at the proximal end of the catheter body and means for deflecting the intermediate section by manipulation of the control handle.

20. A catheter according to claim 19, wherein the control handle comprises a first member fixedly attached to the proximal end of the catheter body and second member that is movable relative to the first member.

21. A catheter according to claim 20, wherein the deflecting means comprises a puller wire having a proximal end and a distal end, the puller wire extending. from the control handle, through the catheter body and into a lumen in the intermediate section, wherein the distal end of the puller wire is fixedly secured within the intermediate section and the proximal end of the puller wire is fixedly secured to the second member of the control handle, whereby manipulation of the first member of the control handle relative to the second member of the control handle moves the puller wire relative to the catheter body, resulting in deflection of the intermediate section.

22. A catheter according to claim 6, further comprising a location sensor mounted within the ablation assembly.

23. A catheter according to claim 22, wherein the location sensor is an electromagnetic location sensor.

24. A catheter according to claim 22, wherein the location sensor is mounted within the distal non-conductive covering.

25. A catheter according to claim 22, further comprising a sensor cable having a distal end fixedly attached to the location sensor, the sensor cable extending through the non-conductive protective tubing, through a lumen in the intermediate section and through the catheter body.

26. A catheter according to claim 6, wherein the ablation assembly forms an angle $\alpha$ ranging from about 60° to about 140° relative to the catheter body.

* * * * *

UNITED STATES PATENT AND TRADEMARK OFFICE
CERTIFICATE OF CORRECTION

| | |
|---|---|
| PATENT NO. | : 7,588,568 B2 |
| APPLICATION NO. | : 10/199525 |
| DATED | : September 15, 2009 |
| INVENTOR(S) | : Kristine B. Fuimaono et al. |

Page 1 of 1

It is certified that error appears in the above-identified patent and that said Letters Patent is hereby corrected as shown below:

In the Claims

Column 12, Claim 21, line 59      Delete "." after the extending

Signed and Sealed this

Ninth Day of November, 2010

David J. Kappos
*Director of the United States Patent and Trademark Office*